United States Patent
Nour

(10) Patent No.: US 9,937,287 B2
(45) Date of Patent: Apr. 10, 2018

(54) PULSATILE MEDICAL DEVICE DESIGNED TO BE USED IN EXTRACORPOREAL SURGERY

(75) Inventor: Sayed Nour, Chaville (FR)

(73) Assignees: Sayed Nour, Paris (FR); Pierre Chastanier, Paris (FR)

(*) Notice: Subject to any disclaimer, the term of this patent is extended or adjusted under 35 U.S.C. 154(b) by 65 days.

(21) Appl. No.: 13/139,316

(22) PCT Filed: Dec. 11, 2009

(86) PCT No.: PCT/EP2009/066994
§ 371 (c)(1),
(2), (4) Date: Jul. 14, 2011

(87) PCT Pub. No.: WO2010/066899
PCT Pub. Date: Feb. 17, 2010

(65) Prior Publication Data
US 2011/0282126 A1 Nov. 17, 2011

(30) Foreign Application Priority Data
Dec. 12, 2008 (FR) ....................................... 0858546

(51) Int. Cl.
*A61M 1/10* (2006.01)
*A61M 1/36* (2006.01)

(52) U.S. Cl.
CPC .......... *A61M 1/3667* (2014.02); *A61M 1/107* (2013.01); *A61M 1/1005* (2014.02);
(Continued)

(58) Field of Classification Search
CPC .. A61M 1/1037; A61M 1/1005; A61M 1/107; A61M 1/3666
(Continued)

(56) References Cited

U.S. PATENT DOCUMENTS 4,080,958 A * 3/1978 Bregman et al. ............... 600/16
4,240,409 A * 12/1980 Robinson et al. .............. 600/16
(Continued)

FOREIGN PATENT DOCUMENTS

WO 01/43797 A 6/2001

OTHER PUBLICATIONS

International Search Report for Appln. No. PCT/EP2009/066994 dated Feb. 18, 2010.

*Primary Examiner* — Eric D. Bertram
(74) *Attorney, Agent, or Firm* — Carter, Deluca, Farrell & Schmidt, LLP

(57) ABSTRACT

The invention relates to a pulsatile medical device enabling a blood flow to be circulated including
  an external pipe presenting an inside wall, an outside wall, and two ends, one end being for connection to an ECC type machine, to a cardiac assistance system or to the patient's body, and one end being for connection to the patient's body;
  an internal pipe inserted in said external pipe and presenting an inside wall, an outside wall, and two ends fastened all around their peripheries to the external pipe all around its periphery, the blood flow passing through said internal pipe;
  the outside wall of the internal pipe and the inside wall of the external pipe defining a space for filling with fluid and being connectable via a connector port to an appliance for creating one or more inflations/deflations of said space, thereby creating one or more pulses in the blood flow.

9 Claims, 5 Drawing Sheets

(52) U.S. Cl.
CPC ........... *A61M 1/106* (2013.01); *A61M 1/1006* (2014.02); *A61M 1/1037* (2013.01); *A61M 1/1086* (2013.01)

(58) Field of Classification Search
USPC .......................................................... 600/16
See application file for complete search history.

(56) References Cited

U.S. PATENT DOCUMENTS 4,906,229 A * 3/1990 Wampler ............ A61M 1/1037
                                                          128/DIG. 3
6,030,335 A * 2/2000 Franchi ........................... 600/16

* cited by examiner

PULSATILE MEDICAL DEVICE DESIGNED TO BE USED IN EXTRACORPOREAL SURGERY

FIELD OF THE INVENTION

The present invention relates to a pulsatile medical device for use in extracorporeal surgery and in other cardiac assistance systems using a pneumatic or an electric pump as a source. By way of example, the device enables regular pulsatile perfusion to be obtained in the organism of a patient being subjected to open heart surgery, or suffering from heart failure.

The cardiovascular system is a closed hydraulic circuit under pressure and that is internally lined with endothelial cells. The endothelium is continuously subjected to tangential shear stress forces that are essential for maintaining the endothelial function that includes vascular tonus by nitride oxide synthesis (NOS), blood coagulation, the inflammatory response, arteriosclerosis, angiogenesis, and apoptosis.

An extracorporeal circulation (ECC) is a medical device that is used to take the place of the heart and the lungs in operating blocks, cardiac catheterization laboratories, or intensive care units, for pediatric or adult patients.

As an energy source, the ECC console is a mathematical model designed on the basis of the laws of physics that govern the movement of a fluid in a closed circuit. Specifically, the circuit is made up of a pump, a heat exchanger, a flow meter, an analyzer of gas and of blood electrolytes, and a pressure recorder, together with biocompatible equipment such as tubes, arterial and venous cannulas, the venous reservoir, the oxygenator, and the arterial filter.

Usually a centrifugal or peristaltic pump is used as the arterial head pump and four other peristaltic pumps are used for cardiotomy suction, heart chamber circulation, the administration of cardioplegia, and an emergency pump.

ECC is necessary for maintaining perfusion of organs and metabolic functions during surgical cardioplegia, or to assist the failing heart muscle until it recovers, or as a relay prior to transplantation.

BACKGROUND OF THE INVENTION

In spite of the progress made in the ECC field since it appeared early 1950s, it still presents drawbacks that give rise to postoperative hemodynamic disorders.

The artificial surfaces of the ECC activate coagulation and platelets, giving rise to a very high probability of clots forming inside the circuit, which can lead to difficult situations such as postoperative bleeding, and biochemical and electrolytic disorders.

The laminar flow in conventional ECC deprives the endothelium of the stimuli of tangential shear stress forces, leading to an endothelial malfunction syndrome that is responsible for activating the complement cascade, the inflammatory response, apoptosis, and hemodynamic disorders, in particular with newborns and children.

The circulation of a fluid in a closed hydraulic circuit (energy transfer with loss of head by friction) depends on the source of energy, the shape of the tubes, and the viscosity and the density of the fluid.

The three main physical laws involved in this mechanism are the following: Newton's law concerning shear force (1668); Bernoulli's third equation concerning energy losses (1738); and Reynolds numbers (1880) that define the density and the movement profile of the liquid.

ECC is based on theories relying on Newtonian fluids at constant viscosity traveling in a closed circuit with unchanging tube geometry.

Cardiovascular circulation contains a non-Newtonian fluid, which moves in vessels that are of variable geometry.

There is thus a confrontation between two different kinds of hydraulic circuit and there are difficulties in adapting them functionally to each other and making them work together harmoniously.

Vascular resistances to cardiovascular circulation are controlled mainly by secreting nitrogen monoxide (NO), and that depends on the endothelial stimulation by shear force. In contrast, in ECC, resistances are more linked to the type of tube, to the oxygenator, to the aortic cannula, to the viscosity, and to the flow being laminar or turbulent.

In practice, this means that it is necessary to quantify the circulatory driving force, whether it be natural (the heart) or artificial (ECC). This circulatory driving force depends on its capacity to move blood with low resistances and thus to maintain vascular tonus and endothelial functions by shear stress, using a regular pulsatile flow including pulse pressure that is physiological.

In order to overcome those drawbacks of conventional ECC, various theoretical strategies have been applied:

the use of medications such as anticoagulants, inotropics, vasodilatators, hormones, electrolytes, blood, platelets, or other substitutes, and this has not completely solved hemodynamic problems while giving rise to specific undesirable effects;

ECC at normal temperature: this is becoming more and more widespread, replacing low temperature ECC. Normal temperature makes blood practically Newtonian, thereby limiting head losses and the inflammatory response, particularly inside the ECC circuit. Nevertheless, its action on the heart and blood vessels is always open to question since the myocardium is protected by cardioplegia injections and microcirculation is facilitated by hemodilution (Fahraeus-Lindqvist) effect;

beating heart surgery without ECC. Beside the beneficial effects on postoperative hemodynamics, such a technique is difficult, and can only be used on patients with few complex needs. It requires specific equipment for holding still the portion on which the operation is being performed, thus making the method expensive;

pulsatile ECC: in order to conserve shear stress stimulation and conserve the endothelial function during surgery, a pulsatile mode of perfusion has been used by various groups over the last three decades. At present, new generations of pulsatile ECC equipment makes use of peristaltic or centrifugal pumps modified for generating a pulsatile perfusion flow. That usually requires two arterial pump heads, one upstream and one downstream from the oxygenator, in order to limit its obstructive effect. That therefore requires special high-technology equipment of high cost, and with mediocre induced pressure curves. Such equipment is therefore not very widespread.

It may be observed that practically all pulsatile machines have been evaluated using Bernoulli's energy loss equations and the perfusion of microcirculation during ECC depends on the hemodilution more than on the type of driving force used. Similarly, it appears paradoxical to apply pulses to a fluid such as blood with its very fragile components in a long rigid tube of small diameter, regardless of the material from which it is made, e.g. polyvinylchloride (PVC) or silicone, and with its undesirable effects of microembolisms.

Another method for obtaining a certain amount of pulsation during conventional ECC (with a continuous flow) is to add an intra-aortic counter-pulsation balloon that is inserted invasively into the thoracic aorta. Although inexpensive and correlated with pulsatile ECC, that method remains invasive, with vascular complications, especially with children or adults suffering from atherosclerosis.

In conclusion, those methods are usually evaluated by the improved perfusion of localized organs such as the renal or splanchnic areas, but provide little protection to distal organs such as cerebral circulation. That creates zones of turbulent shear or Reynolds stress with vortexes close to the walls of blood vessels, vortexes created by two opposing flows meeting, i.e. the laminar ECC flow and the pulsatile flow from the balloon, thereby compromising regional endothelium.

The methods mentioned above thus do not solve the undesirable effects of ECC.

The inventors have proposed a solution in international application WO 2008/000110. That solution consists in a pulsatile tube having a so-called "two-lumen" portion in which the inflatable tube is incorporated in an intra-lumen or extra-lumen manner.

The present invention consists in an improvement of that two-lumen pulsatile tube.

OBJECT AND SUMMARY OF THE INVENTION

The purpose of the improved pulsatile medical device (or tube) of the present invention is to provide a device that generates a flow that is more uniform, minimizing the head losses of the pulsatile flow, particularly in the actual pulsatile zone (see FIG. 6), and to make the use of pulsatile heart assistance systems more widespread as a physiological method of low cost that is easily available and adaptable to the energy sources that are available in medical and surgical services for pediatric patients and also for adults.

The pulsatile medical device of the invention is adaptable to all types of continuous flow cardiac assistance system and may be for single use.

The pulsatile medical device of the invention is a device enabling a blood flow to be circulated and comprising:
  an external pipe presenting an inside wall, an outside wall, and two ends, one end being for connection to an ECC type machine or to a cardiac assistance system or to the patient's body, and one end being for connection to the patient's body;
  an internal pipe inserted in said external pipe, the internal pipe presenting an inside wall, an outside wall, and two ends that are fastened all around their peripheries to the external pipe all around its periphery, the blood flow passing through said internal pipe;
  the outside wall of the internal pipe and the inside wall of the external pipe defining a space for filling with fluid, said space being connectable via a connector port to an appliance for creating one or more inflations/deflations of said space, thereby creating one or more pulses in the blood flow.

A circulating single blood flow having pulsation applied thereto directly makes it possible to create a blood flow that is much uniform and regular than in the prior art. In the prior art, the meeting of a laminar flow coming from the ECC and of a pulsatile flow coming for example from an intra-aortic contra-pulsation balloon, gives rise to vortexes that are not created in the device of the invention. Likewise, head losses are reduced.

In a first embodiment of the invention, the ends of the internal pipe of the pulsatile medical device of the invention are fastened to the inside wall of the external pipe.

The ends of the internal pipe are fastened and sealed using a technique that is equivalent to the endovascular stent technique, namely surgical umbrellas. It is thus possible to use longer lengths of pipe with the advantages of reducing energy loses by eliminating excessive numbers of connections.

In a second embodiment of the invention, the internal pipe is substantially identical in length to the external pipe and the ends of the internal pipe of the pulsatile medical device of the invention are fastened to the outside wall of the external pipe.

The ends of the internal pipe are turned over and sealed externally against the outside wall of the external pipe. This advantageously avoids any risk of gaseous embolism as a result of fluid leakage, using an extracorporeal system.

In a particular embodiment of the invention, a valve is fastened to one or both ends of said internal pipe of the pulsatile medical device of the invention.

The presence of said valve(s) prevents any reflux of the blood flow which can then flow in one direction only. The unidirectional blood flow reduces the vortex effects and head losses.

In a particular embodiment, said space defined between the outside wall of the internal pipe and the inside wall of the external pipe of the pulsatile medical device of the invention is prefilled with fluid.

Because of this prefilling, the use of the device is found to be less costly in terms of energy since the appliance that enables pulsations to be created need only to provide the fluid necessary for compressing this already-filled space (and does not need to be more filled) in order to exert pressure on the blood flow. In this embodiment, the fluid exerts pressure on the outside wall of the external pipe which flexes, and under such circumstances, the external pipe must not be made of rigid material.

In a particular embodiment, the appliance enabling pulsations to be created in the pulsatile medical device of the invention comprises:
  a pouch adapted to be filled with fluid;
  means for compressing the pouch and adapted to compress said pouch in a pulsating manner;
  the connector port connecting said pouch to said space and enabling fluid to flow between said space and said pouch. Such an appliance is described in particular in application FR 08/01818 also belonging to the Applicant.

In another embodiment, the appliance for applying determined pulsatile pressure on a medical device in accordance with the invention comprises:
  means for fluid-taking adapted to take fluid from a high pressure continuous flow fluid source;
  means for tranformating adapted to transform said fluid into a low pressure pulsatile flow fluid;
  at least means for applying said fluid in a low pressure pulsatile flow to said medical device, the connector port connecting said means for applying to said space; and
  means for evacuating said fluid.

Such an appliance is described in particular in application FR 08/02871 also owned by the Applicant.

Preferably, the pulsatile medical device also includes the pouch adapted to be filled with fluid. The pouch may be connected to said pulsatile device during manufacture thereof and/or it may be made integrally therewith, such that it is possible to make available a pulsatile medical device equipped with a pouch, same means for compressing pouch being usable for a plurality of devices according to the invention, each having its respective pouch.

Thus, the pulsatile medical device of the invention (which may also be referred to as tubing), has valves, is prefilled, and is associated with ends made of biocompatible materials, and is therefore likewise suitable for being fastened by direct sutures to heart tissues and to blood vessels. The device which is then associated with an appliance serving to create pulsations of the kind described above constitutes a complete ventricular assistance system on its own.

The system is of low cost and simple to use. It does not require an expensive pressure source such as a pump for an intra-aortic balloon.

The invention also provides a pulsatile medical assembly comprising:

a "Z0" zone comprising an ECC type pump and an oxygenator;
a "Z1" zone comprising a first end of the pulsatile medical device of the invention;
a "Z2" zone comprising a pulsatile medical device of the invention;
a "Z3" zone comprising the second end of the pulsatile medical device of the invention; and
a "Z4" zone comprising an aortic cannula.

The pulsatile medical assembly is a pulsatile heart assistance system that represents a method that is physiological, inexpensive, easily available, and adaptable to energy sources that are available in medical and surgical services both for pediatric patients and also for adults.

In order to analyze the parameters defining the prototype in application of physical laws, so as to explain the improvement in the resulting phenomenon, with energy losses that are minimized, the circuit of the extracorporeal circulation (ECC) circuit is subdivided into six zones:

Z0: comprising an ECC type pump and an oxygenator in which there exists the initial phenomenon as provoked by conventional ECC;

Z1: comprising a first end of the pulsatile medical device of the invention and corresponds to the zone having a regular continuous flow from the oxygenator;

Z2: comprising a pulsatile medical device of the invention, this zone represents the pulsatile portion of the prototype, propulsing stagnant layers from the periphery towards the center and reducing the traumatic effects on the components of blood (red corpuscles);

Z3: comprising the second end of the pulsatile medical device of the invention, this zone represents the zone that actually has a pulsatile flow, i.e. it is the shortest zone of the circuit in order to conserve a maximum amount of pulsatile energy;

Z4: this zone represents the aortic cannula; and

Z5: irrigated tissues of the patient.

The blood flow needs to be transferred from the extracorporeal circulation (ECC) machine to the patient's perfused organs (from Z0 to Z5) while minimizing energy head losses.

To summarize, the assembly of the invention gives rise to reduced energy loses by flow divergence and to reduce hemolytic effects since they occur only in zones Z3 to Z5, whereas in present-day ECC systems, whether pulsatile or otherwise, these losses are spread over Z0 to Z5, with greater amounts of resistance.

In a particular embodiment, the pulsatile medical device of the invention in said pulsatile medical assembly is placed between the oxygenator and the aortic cannula.

In another particular embodiment, the distance represented by the so-called "Z3" zone of said pulsatile medical assembly of the invention is minimized.

Preferably, the portion including the inner and external pipe is adapted to the various dimensions of cardiac assistance systems in terms of length, diameter, volume, and inflation frequency.

BRIEF DESCRIPTION OF THE DRAWINGS

The invention can be better understood with reference to the accompanying drawings, in which.

DETAILED DESCRIPTION

Figure 1:
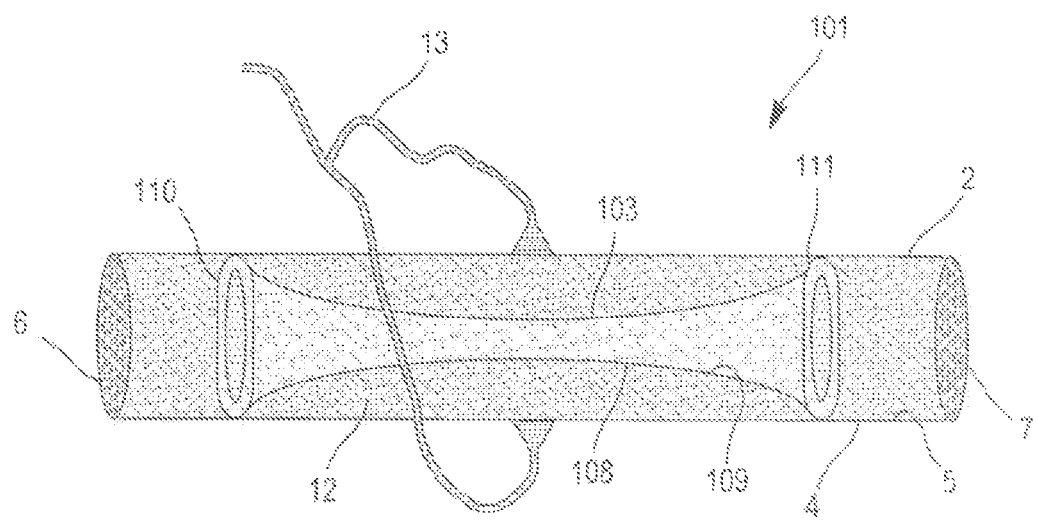
FIG. 1 is a diagram of a first embodiment of a pulsatile medical device of the invention, shown in longitudinal section.

In the drawings, the same reference numbers (units and tens) designate structures that correspond from one figure to another, while the hundreds numbers designate different embodiments.

FIG. 1 shows a first embodiment of a pulsatile medical device 101 of the invention. The device comprises an external pipe 2 in which an internal pipe 103 is inserted. The internal pipe 103 is a compressible pipe made of flexible biocompatible material, such as polyurethane, for example. The external pipe 2 is more rigid, e.g. being made of polyvinyl chloride (PVC) and serves as an outer shell.

The external pipe 2 has an outside wall 4, an inside wall 5, a first end 6 for connection to an ECC type machine, for example, and a second end 7 for connection to the body of a patient. The internal pipe 103 also has an outside wall 108 and an inside wall 109 as well as ends 110 and 111. The internal pipe 103 in FIG. 1 is shorter than the external pipe 2, and the zone where both pipes 2 and 103 are present is a zone referred to as a "two-lumen" zone. In the embodiment of FIG. 1, the ends 110 and 111 of the internal pipe 103 are fastened around their entire periphery to the inside wall 5 of the external pipe 2 over its entire periphery. Thus, a space 12, referred to as a fluid reservoir, is created between the inside wall 5 of the external pipe 2 and the outside wall 108 of the internal pipe 103 in the two-lumen zone. A connector port 13 is designed to be fastened firstly to said space 12 and secondly to an appliance for creating pulsations (not shown in FIG. 1). The appliance for creating pulsations may, for example, be a rhythmic pneumatic pressure source or an electronic rhythmic system. The connector port 13 may be fastened to the space 12 by one or more orifices present in the external pipe 2. In one embodiment, the orifices may be provided with check valves that are closed when the connector port is not fastened and that open under the pressure of the fluid arriving from the connector port 13 when it is fastened thereto. In FIG. 1, the connector port 13 is fastened at two diametrically opposite positions of the external pipe 2 in the two-lumen zone, however it is clear that fastening in one or more positions could be envisaged.

In operation, the pulsatile medical device 101 is connected firstly to an ECC type machine (at its end 6) and secondly to the body of the patient (at its end 7). The connector port 13 is then fastened firstly to the pulsatile medical device 101 via the space 12, and secondly to an appliance serving to create pulsations, where the connector port 13 may be fastened after the blood flow has been put into circulation. The blood flow is then put into circulation: it goes from the ECC type machine towards the body of the patient by passing through the external pipe 2 and then the internal pipe 103 via the two-lumen zone and then once more through the external pipe 2 until it reaches the patient's body. The blood flow is then continuous. In order to create pulsations, the appliance for creating pulsations is put into operation: that appliance regularly delivers a fluid (e.g. a gas such as helium or carbon dioxide) that flows through the connector port 13 into the space 12. On reaching the space 12, the fluid fills said space so as to compress the outside wall 108 of the internal pipe 103, the inside wall 5 of the external pipe 2 remaining rigid. As a result the internal pipe 103 is compressed, thereby creating a pulse in the blood flow passing through said internal pipe 103. A control system may be added to said appliance that is used for creating pulsations, and an operator may then program the frequency of the pulsations as well as their force.

Figure 5:
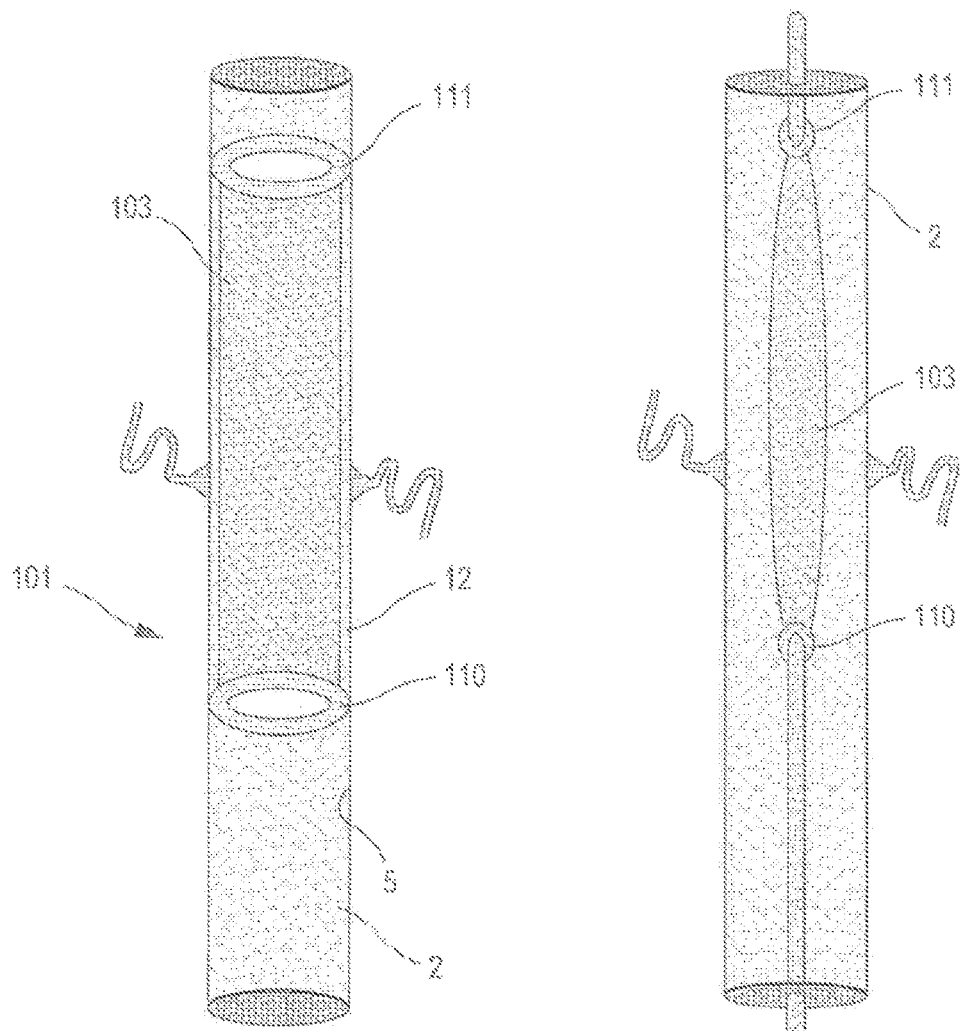
FIGS. 5a and 5b are diagrams of a method of fastening the internal pipe to the external pipe in the embodiment of FIG. 1.

FIGS. 5a and 5b show an example of the method implemented using the internal pipe 103 inside the external pipe 2 in the embodiment of FIG. 1. The internal pipe 103 is inserted inside the external pipe 2 by means of a mandrel 22 in a manner which as such is conventional. Once the internal pipe 103 has been detached from the mandrel 22, the mandrel 22 is removed, with this removal leads to a spreading of the ends 110 and 111 of the internal pipe 103, these ends 110 and 111 becoming pressed against the inside wall 5 of the external pipe 2. The internal pipe 103 is then fastened at each of its ends 110 and 111 by respective spreading umbrellas in a conventional manner.

In a particular embodiment of the invention, the space 12 may be prefilled with an inert fluid. In this embodiment, the appliance for creating pulsations then needs to deliver a quantity of fluid that is less than that needed in the embodiment described below in order to give rise to a pulse. Indeed, the step of filling the space 12 has already been performed. This embodiment of the pulsatile medical device of the invention is thus more compact. Naturally, it must be suitable for being sterilized and packaged.

Figure 2:
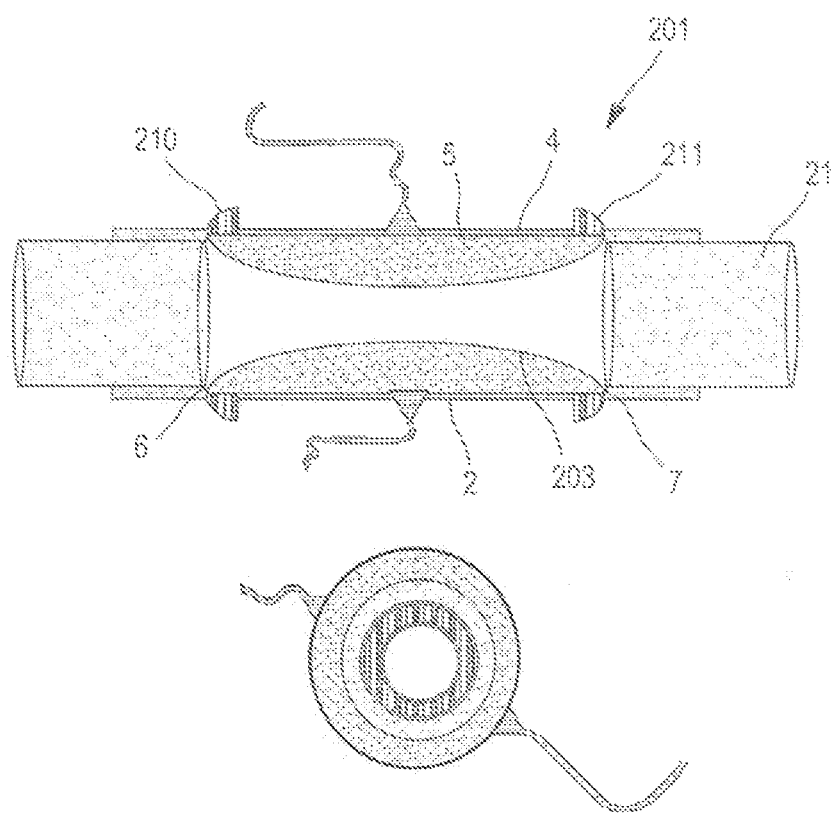
FIG. 2 is a diagram of a second embodiment of a pulsatile medical device of the invention, shown in longitudinal section.

FIG. 2 shows a second embodiment of the pulsatile medical device 201 that is identical with the embodiment of FIG. 1 except that the internal pipe 203 is as long as the external pipe 2, thus making its possible to use a different configuration for the ends 210 and 211 of the internal pipe 203. These ends are not fixed to the inside wall 5 of the external pipe 2, but rather to the outside wall 4 of the external pipe 2 by being folded over. This pulsatile medical device 201 is then fastened at each of its two ends 6/210 and 7/211 to standard ECC connector ports 21 via couplings so as to avoid intravascular accidents in the event of fluid leakage.

Figure 3:
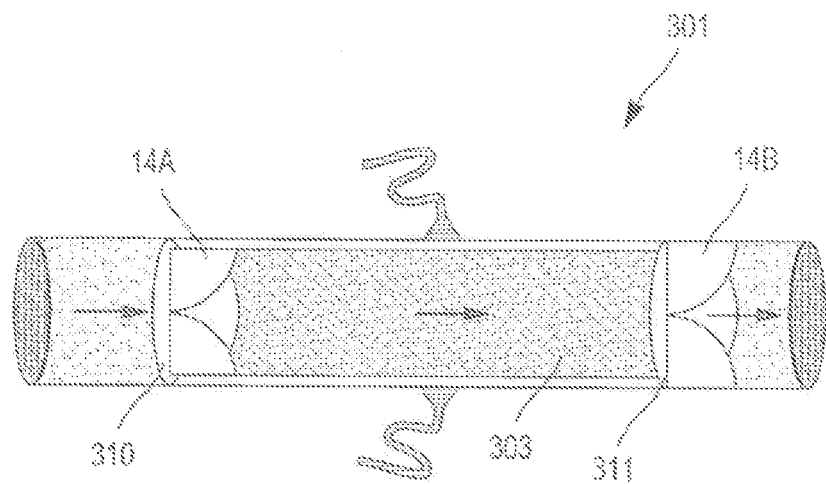
FIG. 3 is a diagram of a third embodiment of a pulsatile medical device of the invention, shown in longitudinal section.

FIG. 3 shows a third embodiment of the pulsatile medical device 301 in which two unidirectional type valves 14A and 14B are placed at the ends 310 and 311 of the internal pipe 303.

The presence of these valves 14A and 14B makes it possible to obtain a unidirectional blood flow (represented by arrows), thereby reducing vortex effects and head losses.

Figure 4:
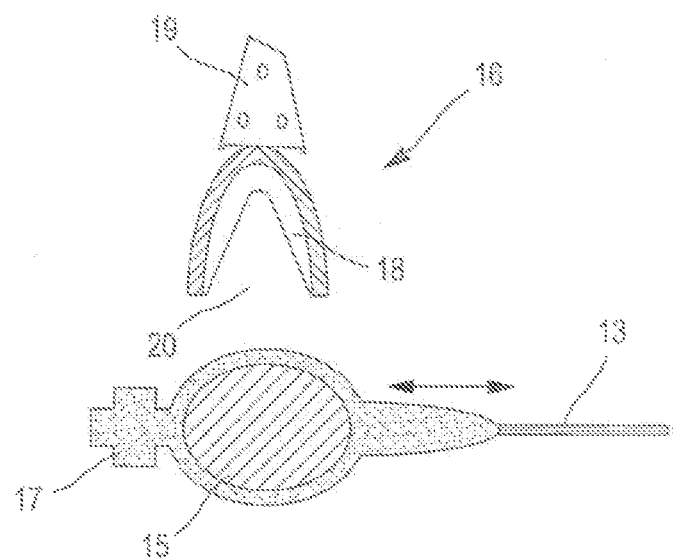
FIG. 4 is a diagram of an example of an appliance suitable for creating pulsation through the pulsatile medical device of the invention.

FIG. 4 shows an example of an appliance for creating pulsations through the pulsatile medical device of the invention. The appliance comprises:
  a first portion including a pouch 15 filled with fluid and connected at one end to the connector port 13 and its other end to an anti-reflux valve 17 enabling the pouch 15 to be filled with fluid or to be emptied; and
  a second portion constituted by means 16 for compressing said pouch 15 and comprising a pouch compressor compartment 18 and a control 19, e.g. electromechanical, for controlling said compressor compartment 18. The compressor compartment 18 has a recess 20.

In operation, the pulsatile medical device of the invention is placed between the body of a patient and an ECC type machine. The connector port 13 is fastened firstly to the pulsatile medical device of the invention (via the space 12) and secondly to the pouch 15. The pouch 15 is filled with fluid by opening the valve 17 (which operation may be performed before connecting the connector port 13 to the pouch 15). The pouch 15 is then placed in the recess 20 of the compressor compartment 18 under the control of the electromechanical control 19. Depending on the instructions received by the electromagnetic control 19, a specific compression/decompression frequency is applied to the pouch 15, which frequency may lie in the range 10 to 300 compressions per minute. Compressing the pouch 15 gives rise to a flow of fluid towards the space 12 that inflates (thereby compressing the internal pipe and creating a pulse in the blood flow), and decompressing the pouch 15 sucks fluid from the space 12 towards the pouch 15, thereby deflating the space 12. The double-headed arrow in FIG. 4 represents the path followed by the fluid. Pulsatile motion of the fluid is thus obtained and thus pulsatile inflation/deflation of the space 12, thereby causing one or more pulses to be formed in the blood flow passing through the internal pipe. It is possible to envisage means for compressing 16 having a system that enables the frequency of the compressions (and thus of the pulses) to be synchronized with the frequency of the patient's heart beats. These means for compressing 16 are inexpensive, and because they are compact, they are also portable.

This example of the means for compressing 16 is particularly adapted to the embodiment of the pulsatile medical device of the invention in which the space 12 is prefilled with fluid.

Figure 6:
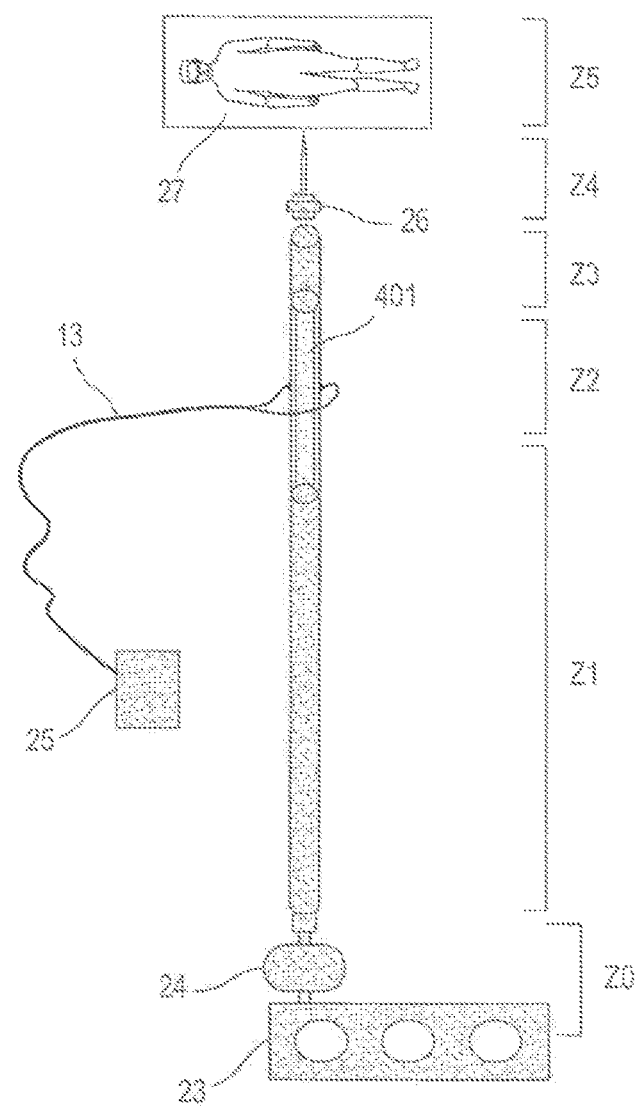
FIG. 6 is a diagram of a pulsatile medical assembly of the invention fitted to a patient.

FIG. 6 is a diagram of the connection between the ECC machine and the patient as occurs during heart surgery or while using a cardiac assistance system. The connection comprises a circuit subdivided into six zones (Z0-Z5). The zone Z0 comprises an ECC type pump 23 and an oxygenator 24, a zone Z1 comprises a first end of the pulsatile medical device 401 (which may be any of the various embodiments described above), the zone Z2 comprises the pulsatile medical device 401 connected via the connector port 13 to an appliance 25 for creating pulsations, the zone Z3 comprises the second end of the pulsatile medical device 401 (this is the actual pulsatile zone), and the zone Z4 comprises an aortic cannula 26. By also including the perfused organs 27 of the patient in a zone Z5, a closed hydraulic circuit is obtained under pressure.

Figure 7:
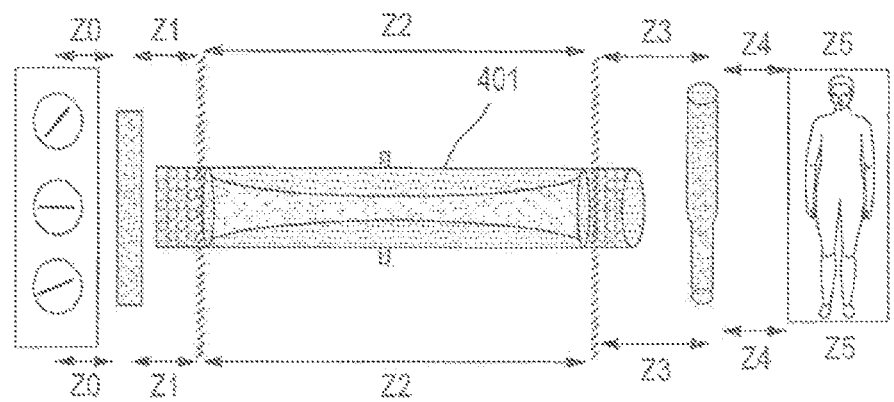
FIG. 7 is a diagram of the head losses in the pulsatile medical assembly of FIG. 6.

FIG. 7 is a diagram of the head losses in the above-defined circuit. Head losses are always present in Z0 and Z4, conventional positions for the oxygenator 24 and the aortic cannula 26, and such losses also exist in Z5 as a result of the vasoconstriction caused by the laminar flow or the inadequate pulsatile perfusion. The three zones Z1, Z2, and Z3 are zones that, by virtue of the pulsatile medical device 401, present minimum head losses. In Z1, the shape of the pulsatile medical device 401, its limits, and its position downstream from the oxygenator 24, enable a laminar flow to flow with low resistance. In Z2, the compression of the internal pipe during a pulse moves the peripheral layers of the blood flow towards the center without creating turbulence and without traumatizing the components of the blood (red corpuscles). The actual pulsatile flow thus begins solely in Z3 as a result of the device of the invention. The distance between the pulsatile medical device and the perfused organs (i.e. the zones Z3, Z4, and Z5) should be minimized (in other words the zone Z3 should be minimized since the other two zones cannot be reduced) in order to conserve the pulsatile pulses with minimum head losses.

In addition to the head losses that are minimized in the zones Z1, Z2, and Z3, by using the pulsatile medical device of the invention, it is possible to envisage reducing the following head losses:
  at the end of the aortic cannula 26 (zone Z4) by using a diverging diffuser with head loss that is gradually corrected by the arterial wall in application of Hagen Poiseuille's formula;
  at Z5 by an appropriate pulsatile flow provided by the device of the invention enabling vasodilatation of the perfused organs by increasing the secretion of NOS.

The reduction in head losses resulting from the device of the invention thus takes place in Z3, Z4, and Z5, whereas in a conventional ECC, whether pulsatile or otherwise, head losses take place in Z0 to Z5, and thus in three additional zones. The device does not require a double perfusion pump, nor does it require a special low resistance oxygenator, unlike other ECCs, in order to reduce head losses. In order to minimize head losses, it is preferable to fabricate the pulsatile medical device of the invention as a single unit. The device gives rise to less turbulence at its ends, to fewer diverging diffusers, where diffusers give rise to head losses, and also to fewer hemolytic effects.

Figure 8A:
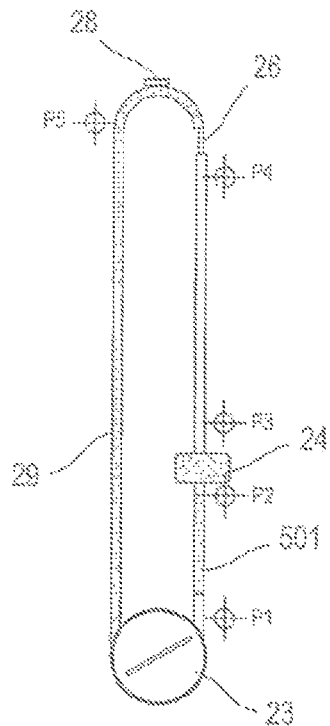
FIGS. 8a, 8b, and 8c are diagrams of circuits representing a pulsatile medical assembly of the invention applied to a resistance that simulates a patient, which resistance is connected, by return, to the pulsatile medical assembly of the invention, thereby creating a closed circuit.
Figure 8B:
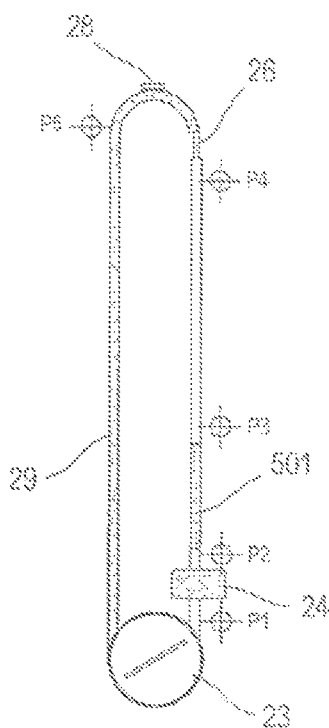
Figure 8C:
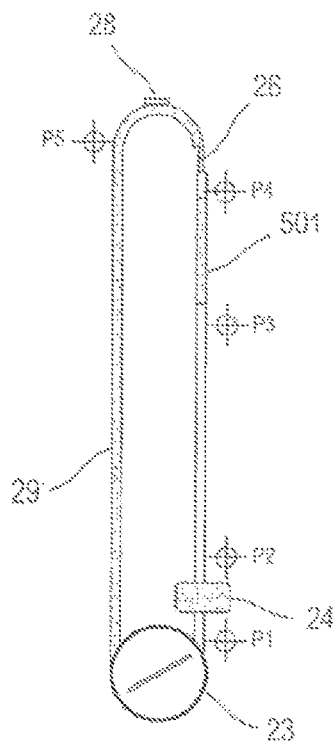

FIGS. 8a, 8b, and 8c are diagrams of models of the circuit of an ECC machine together with a patient as shown in FIG. 6. In these models, the perfused organs of the patient are simulated by a resistance 28. In these three variants of the circuit, there can be seen the same elements as those shown in FIGS. 6 and 7, i.e. the ECC type pump 23 [the ECC circuit being made of PVC with a diameter of 0.63 centimeters (cm) (one-quarter of an inch)] and the oxygenator 24 (with filter), the pulsatile medical device of the invention 501 (possibly being any of the variant embodiments described above), the aortic cannula 26 (of size 14) and a resistance 28 simulating the upstream vascular resistance of the perfused organs. In order to obtain a closed circuit, and thus properly minimize the blood flow, a silicone return 29 is provided that connects the resistance 28 to the ECC type pump 23. In tests, fluid was then set into circulation in this circuit (in the direction ECC pump-oxygenator-resistance) and the pulsations of the medical device 501 of the invention were put into operation. The pressures were then measured at P1, P2, P3, P4, and P5 (fixed locations in the circuit).

The difference between the three variant models of FIGS. 8a, 8b, and 8c lies in the position of the pulsatile medical device 501: upstream from the oxygenator in FIG. 8a, and downstream from the oxygenator in FIGS. 8b and 8c (the distance between the device 501 and the resistance 28 simulating the perfused organs of the patient being minimized in FIG. 8c).

The results of those pressure measurements (in mmHg) are set out in the tables below.

| FIG. 8c | | |
|---|---|---|
| Pressure | Constant* | Pulsatile** |
| P1 | 31 | 160 |
| P2 | 28 | 150 |
| P3 | 27 | 156 |
| P4 | 24 | 132 |
| P5 | 19 | 93 |

*Device 501 not subjected to pulsations.
**Device 501 subjected to pulsations.

| FIG. 8b | | |
|---|---|---|
| Pressure | Constant* | Pulsatile** |
| P1 | 32 | 128 |
| P2 | 27 | 119 |
| P3 | 26 | 183 |
| P4 | 17 | 129 |
| P5 | 18 | 72 |

*Device 501 not subjected to pulsations.
**Device 501 subjected to pulsations.

| FIG. 8a | | |
|---|---|---|
| Pressure | Constant* | Pulsatile** |
| P1 | 47 | 234 |
| P2 | 28 | 121 |
| P3 | 21 | 92 |
| P4 | 17 | 53 |
| P5 | 19 | 51 |

*Device 501 not subjected to pulsations.
**Device 501 subjected to pulsations.

The head losses recorded were smaller in the configuration of FIG. 8c, i.e. when the pulsatile medical device 501 of the invention was placed downstream from the oxygenator 24 and at a minimum distance from the perfused organs of the patient.

Naturally, the invention is not limited to the embodiments described and shown. Thus, for example, a pulsatile medical device of the invention may present valves and may be connected to an appliance serving to create pulsations of the type described with reference to FIG. 4.

What is claimed is:
1. An extracorporeal pulsatile medical device disposed between a patient's body and an extracorporeal circulation (ECC) type machine, for enabling a blood flow to be circulated, wherein the device comprises:
  an external pipe defining a first length and presenting an inside wall that defines a first lumen having a first diameter, an outside wall, and two ends, a proximal one of the two ends being connected to an oxygenator and an ECC type machine or a cardiac assistance system, and a distal one of the two ends being for connection to a patient's body;

an internal pipe defining a second length greater than the first length, the internal pipe inserted in said first lumen of said external pipe, the internal pipe defining a body portion presenting an inside wall that defines a second lumen having a second diameter smaller than the first diameter, and an outside wall, the internal pipe including two ends that are flared radially outwardly relative to a largest diameter of the body portion and directly fastened all around their peripheries to the outside wall of the external pipe all around its periphery, the blood flow passing through said internal pipe;

the outside wall of the body portion of the internal pipe and the inside wall of the external pipe defining a space for filling with fluid, said space being connectable via a connector port to an appliance for creating one or more inflations/deflations of said space, thereby creating one or more pulsations in the blood flow; and said connector port being connected to said space via at least two orifices formed through said external pipe at at least two diametrically opposite positions.

2. The extracorporeal pulsatile medical device according to claim 1, wherein a valve is fastened to and placed at one or both ends of said internal pipe.

3. The extracorporeal pulsatile medical device according to claim 1, wherein said space is prefilled with fluid.

4. The extracorporeal pulsatile medical device according to claim 1, wherein the appliance serving to create pulsation comprises:

a pouch adapted to be filled with fluid;

means for compressing the pouch and adapted to compress said pouch in a pulsating manner;

the connector port connecting said pouch to said space and enabling fluid to flow between said space and said pouch.

5. The extracorporeal pulsatile medical device according to claim 1, wherein the appliance enabling pulsations to be created comprises:

means for fluid-taking adapted to take fluid from a high pressure continuous flow fluid source;

means for transformating adapted to transform said fluid into a low pressure pulsatile flow fluid;

at least means for applying said fluid in a low pressure pulsatile flow to said medical device, the connector port connecting said means for applying to said space; and means for evacuating said fluid.

6. The extracorporeal pulsatile medical device according to claim 1, wherein the external pipe has an unchanging tube geometry.

7. A pulsatile medical assembly comprising:

a "Z0" zone comprising the ECC type pump and the oxygenator;

a "Z1" zone comprising a first end of an extracorporeal pulsatile medical device according to claim 1;

a "Z2" zone comprising the extracorporeal pulsatile medical device according to claim 1;

a "Z3" zone comprising the second end of the extracorporeal pulsatile medical device according to claim 1; and a "Z4" zone comprising an aortic cannula.

8. The pulsatile medical assembly according to claim 7, wherein the pulsatile medical device is placed between the oxygenator and the aortic cannula.

9. The pulsatile medical assembly according to claim 7, wherein the distance represented by said "Z3" zone is reduced to a minimum.

* * * * *